US00PP31086P2

(12) United States Plant Patent
Olesen et al.

(10) Patent No.: US PP31,086 P2
(45) Date of Patent: Nov. 19, 2019

(54) ***CLEMATIS* PLANT NAMED 'EVIPO090'**

(50) Latin Name: *Clematis viticella*
Varietal Denomination: Evipo090

(71) Applicants: Mogens Nyegaard Olesen, Fredensborg (DK); Raymond J. Evison, St Sampsons Vale (GB)

(72) Inventors: Mogens Nyegaard Olesen, Fredensborg (DK); Raymond J. Evison, St Sampsons Vale (GB)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 15/999,909

(22) Filed: Sep. 10, 2018

(51) Int. Cl.
*A01H 5/00* (2018.01)
*A01H 6/72* (2018.01)

(52) U.S. Cl.
USPC ..... Plt./228
CPC ..... *A01H 6/72* (2018.05)

(58) Field of Classification Search
USPC ..... Plt./228
CPC ..... A01H 5/02; A01H 5/00
See application file for complete search history.

(56) References Cited

PUBLICATIONS https://www.rhs.org.uk/plants/pdfs/plant-register-supplements/Clematis/6th-Clematis-Supplement.pdf; 2018; 1 page.*

* cited by examiner

*Primary Examiner* — Kent L Bell

(57) ABSTRACT

A new *Clematis* plant with a compact growth habit, profuse, violet purple flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

1 Drawing Sheet

Botanical classification:
Genus: *Clematis.*
Species: *viticella.*
Variety denomination: 'Evipo090'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both parent varieties are non-patented.

The two parents were crossed during the summer of 2006 and the resulting seeds were planted the following winter in a controlled environment in Guernsey, Channel Islands, United Kingdom. The new variety named 'Evipo090' originated as a single seedling from the stated cross.

The new *clematis* plant may be distinguished from its female seed parent and male pollen parent by the following characteristics. The female seed parent grows to 200 cm in height, while the new variety grows to 130 cm in height. The male seed parent has Purple Group N79C flowers while the new variety has Violet 83A tepals.

The objective of the hybridization of this *clematis* plant was to create a new and distinct variety for nursery culture with unique qualities such as:

1. Uniform and abundant violet purple flowers;
2. Vigorous and compact growth, making the variety suitable for container culture; and
3. Improved disease resistance.

This combination of qualities was lacking in *clematis* plants that were in commercial cultivation and the qualities have been substantially achieved in the new variety.

'Evipo090' was selected by Mogens N. Olesen and Raymond J. Evison in their *clematis* development program in the Channel Islands, United Kingdom in 2007. Asexual reproduction of 'Evipo090' by means of vegetative cuttings and traditional layering was first performed by Mogens N. Olesen and Raymond J. Evison in the nursery during the summer of 2007. This initial and subsequent asexual propagations have demonstrated that the characteristics of 'Evipo090' are true to type and are transmitted from one generation to the next.

BRIEF DESCRIPTION OF THE DRAWING

The accompanying color illustration shows as true as is reasonably possible to obtain in color photographs of this type the typical characteristics of the buds, flowers, leaves, and stems, of 'Evipo090'. Specifically illustrated in the drawing is an open flower, tepals detached showing reproductive flower parts, flower buds, leaves, stems, and seed head. Illustrated plants are 2 years of age.

DETAILED DESCRIPTION OF THE VARIETY

The following is a detailed description of 'Evipo090', as observed in its growth throughout the flowering period in Denmark. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *clematis* variety 'Evipo042' described and illustrated in U.S. Plant Pat. No. 24,172 are compared to 'Evipo090' in Chart 1.

CHART 1

| | 'Evipo090' | 'Evipo042' |
|---|---|---|
| Flower diameter | 85 to 100 mm | 170 mm |
| Tepal upper surface | Violet Group 83A | Violet Group 83A at margins and Purple-Violet Group N80B at the mid-section |
| Tepal count | 5 to 6 | 7 |

FLOWER AND FLOWER BUD

Blooming habit: Recurrent. The natural flowering period is generally from April to September.

Flower bud:
- *Size*.—Normally 25 mm in length. Bud diameter is 10 mm.
- *Bud form*.—Long, elliptic, and broad based.
- *Bud color*.—Yellow-Green Group 145B and Violet Group 83C.
- *Texture*.—Pubescent.

Pedicel:
- *Surface texture*.—Smooth.
- *Length*.—12 to 25 mm in length with 2 mm diameter.
- *Color*.—Yellow-Green Group 145A.
- *Strength*.—Moderately strong.

Receptacle:
- *Surface texture*.—Lightly pubescent.
- *Shape*.—Broad funnel.
- *Size*.—1 mm (h)×3 mm (w).
- *Color*.—Yellow-Green Group 145A.

Flower arrangement:
- *Location on vine*.—New growth only.
- *Borne*.—Singly, emerging from each leaf axillary.

Flower bloom:
- *Size*.—On average, flowers are 85 to 100 mm in diameter and 15 mm in depth.
- *Profile*.—Open flowers are flat, somewhat convex.
- *Fragrance*.—None.
- *Lasting quality*.—Flowers normally remain up to 10 days on the plant.

Tepals:
- *Tepal color*.—Upon opening, the upper surface is Violet Group 83A. The lower surface is Violet-Blue 90C with a stripe of Yellow-Green Group 144C. After opening, the upper surface is Violet Group 83A. The lower surface is Violet-Blue 90C with a stripe of Yellow-Green Group 145C.
- *Quantity*.—Normally 5 to 6 tepals.
- *Size*.—40-45 mm in length by 25-32 mm wide.
- *Shape*.—Individual tepal shape is lanceolate. The tepal apex is acuminate. The tepal base acute.
- *Apex recurvature*.—Slight.
- *Tepal cross section*.—Flat and slightly cupped.
- *Margins*.—Entire.
- *Persistence*.—Tepals drop off cleanly.

Reproductive organs:
- *Pollen*.—Quantity: Average. Color: Yellow Group 4B.
- *Anthers*.—Size: 4 mm in length. Color: Violet Group 83B. Quantity: On average, 80.
- *Filaments*.—Color: Violet Group 85C. Length: 8 mm.
- *Pistils*.—Quantity: On average, 35.
- *Stigmas*.—Inferior in location relative to the length of the filaments and the height of the anthers. Color: Violet Group 83A.
- *Styles*.—Color: Yellow-Green Group 145C. Length: 5 mm.

Seed head characteristics:
- *Size*.—40 mm in height. 40 mm in diameter.
- *Quantity*.—The average number of seeds produced per seed head is 35.
- *Style appearance*.—Plumose, semi-erect.

PLANT

Plant form: Climbing.

Plant growth: Vigorous.

Size: Seasons growth attains 130 cm in height. Average spread is 70 cm.

Stems:
- *Color*.—Juvenile stems are Greyed-Purple Group 183A. Mature stems are Greyed-Purple Group 183A.
- *Internodes*.—On average, 8 cm between nodes.
- *Length*.—Normally 50 cm from the base of the plant to the flowering portion of the stem.
- *Diameter*.—About 2 or 3 mm.
- *Texture*.—Mature stems are ribbed.

Plant foliage:
- *Leaf characteristics*.—Deciduous/Evergreen.
- *Arrangement*.—Ternate.
- *Leaf size*.—Compound leaves are 70 to 120 mm (l)×60 to 140 mm (w). Leaflets are about 60 mm (l)×35 mm (w).
- *Abundance*.—1 or 2 leaves per 10 cm of stem.
- *Leaf color*.—Juvenile upper Yellow-Green Group 144A. Juvenile lower Green Group 138B. Mature upper Yellow-Green Group 147A. Mature lower Yellow-Green Group 147B.
- *Stipules*.—Absent.
- *Petioles*.—Size: 30 to 55 mm in length by 2 mm diameter. Texture: Smooth. Color: Greyed-Orange Group 166A.
- *Petioloule*.—Size: 3 to 30 mm in length by 2 mm diameter. Texture: Smooth. Color: Greyed-Orange Group 166A.
- *Leaflet shape*.—Ovate, elliptic. The base is rounded, apex acute.
- *Margin*.—Entire.
- *Surface*.—The upper side is smooth, the lower side is smooth.
- *Thickness*.—Moderate.
- *Glossiness*.—Not glossy.

Disease resistance: Subject to any disease that normally attacks the species. However the variety is more tolerant to *clematis* wilt, *Ascochyta clematidina*, than some *clematis* known to the inventors.

Cold hardiness: The variety is tolerant to USDA Hardiness Zone 6.

Heat tolerance: The variety has been found to be suitable for climate conditions found in the American Horticulture Society heat zone 7.

We claim:

1. A new and distinct variety of *clematis* plant named 'Evipo090', substantially as described and illustrated, due to its abundant violet purple flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

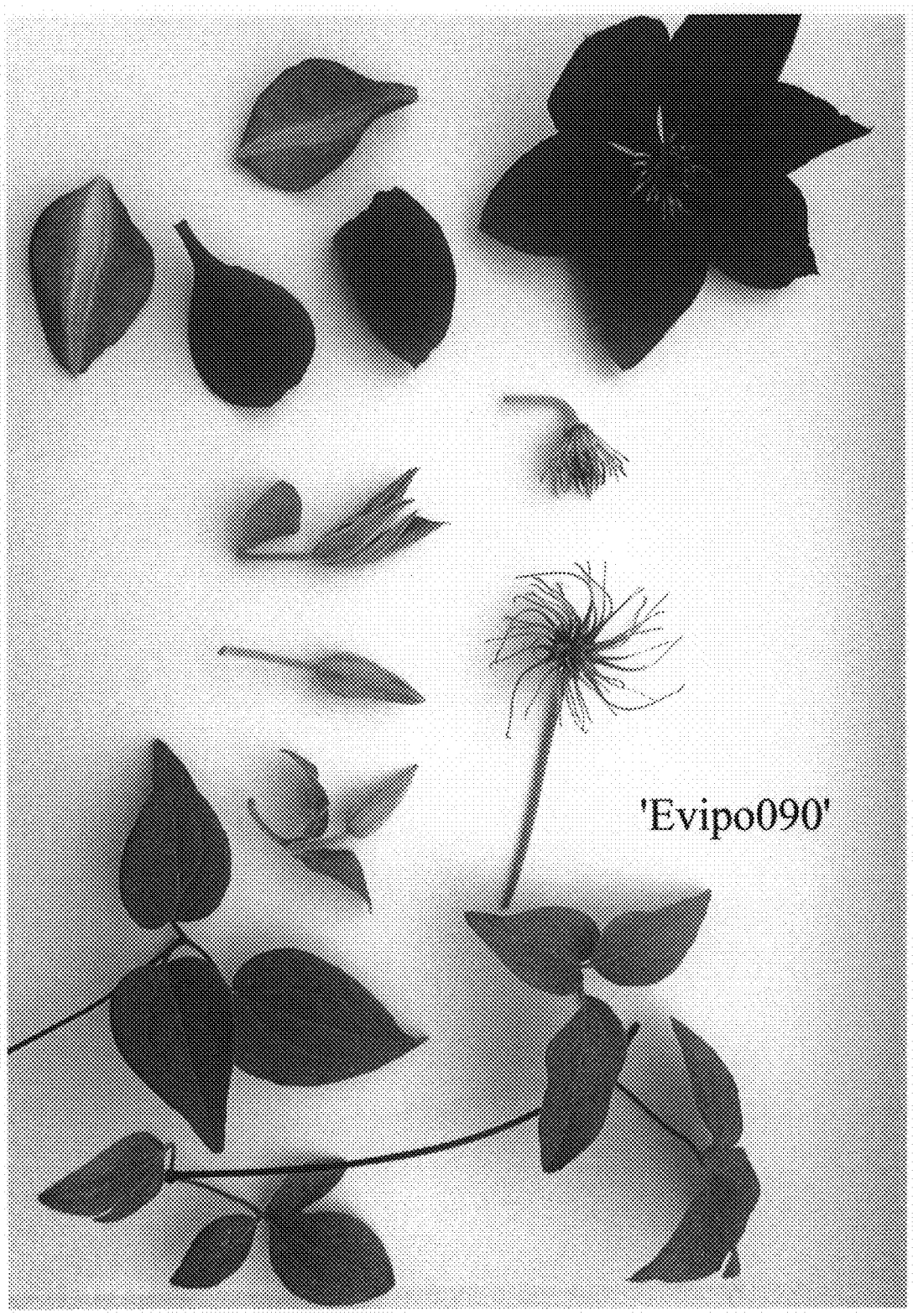
'Evipo090'